United States Patent
Burnett et al.

(10) Patent No.: US 9,622,670 B2
(45) Date of Patent: Apr. 18, 2017

(54) METHOD AND APPARATUS FOR PRESSURE MEASUREMENT

(75) Inventors: Daniel Rogers Burnett, San Francisco, CA (US); Byron Reynolds, Gilroy, CA (US); Brian M. Neil, San Francisco, CA (US); Gregory W. Hall, Los Gatos, CA (US); Paul B. Guerra, Los Gatos, CA (US)

(73) Assignee: Potrero Medical, Inc., San Francisco, CA (US)

( * ) Notice: Subject to any disclaimer, the term of this patent is extended or adjusted under 35 U.S.C. 154(b) by 1065 days.

(21) Appl. No.: 13/809,043

(22) PCT Filed: Jul. 11, 2011

(86) PCT No.: PCT/US2011/043570
§ 371 (c)(1),
(2), (4) Date: Apr. 1, 2013

(87) PCT Pub. No.: WO2012/006625
PCT Pub. Date: Jan. 12, 2012

(65) Prior Publication Data
US 2013/0231584 A1 Sep. 5, 2013

Related U.S. Application Data

(60) Provisional application No. 61/399,298, filed on Jul. 9, 2010, provisional application No. 61/393,794, filed on Oct. 15, 2010.

(51) Int. Cl.
*A61B 5/00* (2006.01)
*A61B 5/03* (2006.01)
(Continued)

(52) U.S. Cl.
CPC ............ *A61B 5/036* (2013.01); *A61B 5/20* (2013.01); *A61B 5/205* (2013.01); *A61B 5/412* (2013.01);
(Continued)

(58) Field of Classification Search
CPC .. A61B 5/03; A61B 5/036; A61B 5/20; A61B 5/205; A61B 5/412; A61B 5/02055;
(Continued)

(56) References Cited

U.S. PATENT DOCUMENTS 2,078,786 A 4/1937 Wood
3,042,042 A 7/1962 Blanck
(Continued)

FOREIGN PATENT DOCUMENTS

CN 1094605 A 2/1994
CN 1146728 A 2/1996
(Continued)

OTHER PUBLICATIONS

Burnett et al.; U.S. Appl. No. 13/937,102 entitled "Automated Therapy System and Method" filed Jul. 8, 2013.
(Continued)

*Primary Examiner* — Max Hindenburg
(74) *Attorney, Agent, or Firm* — Levine Bagade Han LLP

(57) ABSTRACT

Methods and apparatus for measuring pressure in a patient are provided which may include any number of features. One feature is a pressure measurement system comprising a pressure source, a compliant bladder, a catheter in communication with the pressure source, pressure sensors, and a controller configured to determine a pressure within the compliant bladder. The pressure measurement system can inflate the compliant bladder with gas or air to determine a
(Continued)

pressure within a patient. In one embodiment, the pressure measurement system measures pressure within a peritoneal cavity.

20 Claims, 6 Drawing Sheets

(51) Int. Cl.
*A61B 5/20* (2006.01)
*A61M 25/10* (2013.01)
*A61B 5/0205* (2006.01)
*A61B 5/0215* (2006.01)
*A61B 5/145* (2006.01)

(52) U.S. Cl.
CPC ......... *A61B 5/0215* (2013.01); *A61B 5/02055* (2013.01); *A61B 5/14539* (2013.01); *A61B 5/14542* (2013.01); *A61B 5/14546* (2013.01); *A61B 5/6853* (2013.01); *A61M 25/1018* (2013.01)

(58) Field of Classification Search
CPC .............. A61B 5/0215; A61B 5/14539; A61B 5/14542; A61B 5/14546; A61B 5/6853; A61M 25/1018; A61M 25/10184
See application file for complete search history.

(56) References Cited

U.S. PATENT DOCUMENTS

| | | |
|---|---|---|
| 3,505,988 A | 4/1970 | Deane |
| 3,698,396 A | 10/1972 | Katerndahl et al. |
| 3,927,980 A | 12/1975 | Leonard |
| 4,302,972 A | 12/1981 | Oettle et al. |
| 4,356,826 A | 11/1982 | Kubota |
| 4,413,633 A | 11/1983 | Yanda |
| 4,424,806 A | 1/1984 | Newman et al. |
| 4,445,500 A | 5/1984 | Osterholm |
| 4,450,841 A | 5/1984 | Osterholm |
| 4,497,324 A | 2/1985 | Sullivan et al. |
| 4,535,773 A | 8/1985 | Yoon |
| 4,808,157 A | 2/1989 | Coombs |
| 4,813,429 A | 3/1989 | Eshel et al. |
| 4,883,459 A | 11/1989 | Calderon |
| 4,904,237 A | 2/1990 | Janese |
| 4,919,134 A | 4/1990 | Streeter |
| 4,963,130 A | 10/1990 | Osterholm |
| 5,108,364 A | 4/1992 | Takezawa et al. |
| 5,122,267 A | 6/1992 | Giovanetti et al. |
| 5,141,492 A | 8/1992 | Dadson et al. |
| 5,141,493 A | 8/1992 | Jacobsen et al. |
| 5,149,321 A | 9/1992 | Klatz et al. |
| 5,245,367 A | 9/1993 | Miller et al. |
| 5,249,585 A | 10/1993 | Turner et al. |
| 5,261,891 A | 11/1993 | Brinkerhoff et al. |
| 5,344,136 A | 9/1994 | Capdeboscq |
| 5,354,277 A | 10/1994 | Guzman et al. |
| 5,380,160 A | 1/1995 | Chen |
| 5,395,342 A | 3/1995 | Yoon |
| 5,433,216 A | 7/1995 | Sugrue et al. |
| 5,478,329 A | 12/1995 | Ternamian |
| 5,554,280 A | 9/1996 | Loehr |
| 5,562,821 A | 10/1996 | Gutierrez-Collazo |
| 5,573,007 A | 11/1996 | Bobo, Sr. |
| 5,623,940 A | 4/1997 | Daikuzono |
| 5,665,227 A | 9/1997 | Watt |
| 5,693,017 A | 12/1997 | Spears et al. |
| 5,709,654 A | 1/1998 | Klatz et al. |
| 5,709,661 A | 1/1998 | Van Egmond et al. |
| 5,730,720 A | 3/1998 | Sites et al. |
| 5,752,929 A | 5/1998 | Klatz et al. |
| 5,755,668 A | 5/1998 | Itoigawa et al. |
| 5,755,756 A | 5/1998 | Freedman, Jr. et al. |
| 5,837,003 A | 11/1998 | Ginsburg |
| 5,916,153 A | 6/1999 | Rhea, Jr. |
| 5,951,497 A | 9/1999 | Wallace et al. |
| 5,984,879 A | 11/1999 | Wallace et al. |
| 6,019,729 A | 2/2000 | Itoigawa et al. |
| 6,019,783 A | 2/2000 | Philips et al. |
| 6,056,766 A | 5/2000 | Thompson et al. |
| 6,066,163 A | 5/2000 | John |
| 6,117,076 A | 9/2000 | Cassidy |
| 6,122,536 A | 9/2000 | Sun et al. |
| 6,126,684 A | 10/2000 | Gobin et al. |
| 6,146,411 A | 11/2000 | Noda et al. |
| 6,149,624 A | 11/2000 | McShane |
| 6,149,670 A | 11/2000 | Worthen et al. |
| 6,165,207 A | 12/2000 | Balding et al. |
| 6,175,688 B1 | 1/2001 | Cassidy et al. |
| 6,188,930 B1 | 2/2001 | Carson |
| 6,197,045 B1 | 3/2001 | Carson |
| 6,231,524 B1 | 5/2001 | Wallace et al. |
| 6,231,594 B1 | 5/2001 | Dae |
| 6,254,567 B1 | 7/2001 | Treu et al. |
| 6,261,312 B1 | 7/2001 | Dobak, III et al. |
| 6,264,680 B1 | 7/2001 | Ash |
| 6,287,326 B1 | 9/2001 | Pecor |
| 6,290,717 B1 | 9/2001 | Philips |
| 6,299,599 B1 | 10/2001 | Pham et al. |
| 6,304,776 B1 | 10/2001 | Muntermann |
| 6,312,452 B1 | 11/2001 | Dobak, III et al. |
| 6,336,910 B1 | 1/2002 | Ohta et al. |
| 6,338,727 B1 | 1/2002 | Noda et al. |
| 6,368,304 B1 | 4/2002 | Aliberto et al. |
| 6,375,674 B1 | 4/2002 | Carson |
| 6,379,331 B2 | 4/2002 | Barbut et al. |
| 6,405,080 B1 | 6/2002 | Lasersohn et al. |
| 6,409,699 B1 | 6/2002 | Ash |
| 6,419,643 B1 | 7/2002 | Shimada et al. |
| 6,436,295 B2 | 8/2002 | Kim |
| 6,447,474 B1 | 9/2002 | Balding |
| 6,450,990 B1 | 9/2002 | Walker et al. |
| 6,451,045 B1 | 9/2002 | Walker et al. |
| 6,458,150 B1 | 10/2002 | Evans et al. |
| 6,460,544 B1 | 10/2002 | Worthen |
| 6,461,379 B1 | 10/2002 | Carson et al. |
| 6,480,257 B2 | 11/2002 | Cassidy et al. |
| 6,497,721 B2 | 12/2002 | Ginsburg et al. |
| 6,520,933 B1 | 2/2003 | Evans et al. |
| 6,529,775 B2 | 3/2003 | Whitebook et al. |
| 6,530,945 B1 | 3/2003 | Noda et al. |
| 6,530,946 B1 | 3/2003 | Noda et al. |
| 6,547,811 B1 | 4/2003 | Becker et al. |
| 6,551,302 B1 | 4/2003 | Rosinko et al. |
| 6,554,797 B1 | 4/2003 | Worthen |
| 6,572,640 B1 | 6/2003 | Balding et al. |
| 6,579,496 B1 | 6/2003 | Fausset et al. |
| 6,581,403 B2 | 6/2003 | Whitebook et al. |
| 6,582,398 B1 | 6/2003 | Worthen et al. |
| 6,585,692 B1 | 7/2003 | Worthen |
| 6,592,577 B2 | 7/2003 | Abboud et al. |
| 6,592,612 B1 | 7/2003 | Samson et al. |
| 6,602,243 B2 | 8/2003 | Noda |
| 6,620,187 B2 | 9/2003 | Carson et al. |
| 6,620,189 B1 | 9/2003 | Bloom et al. |
| 6,632,196 B1 * | 10/2003 | Houser .................. A61B 5/036 604/93.01 |
| 6,635,053 B1 | 10/2003 | Lalonde et al. |
| 6,638,265 B1 | 10/2003 | Ternamian |
| 6,641,602 B2 | 11/2003 | Balding |
| 6,641,603 B2 | 11/2003 | Walker et al. |
| 6,645,232 B2 | 11/2003 | Carson |
| 6,645,234 B2 | 11/2003 | Evans et al. |
| 6,648,905 B2 | 11/2003 | Record et al. |
| 6,660,027 B2 | 12/2003 | Gruszecki et al. |
| 6,669,715 B2 | 12/2003 | Hoglund et al. |
| 6,673,098 B1 | 1/2004 | Machold et al. |
| 6,676,409 B2 | 1/2004 | Grant |
| 6,676,689 B2 | 1/2004 | Dobak, III et al. |
| 6,682,551 B1 | 1/2004 | Worthen et al. |
| 6,685,733 B1 | 2/2004 | Dae et al. |
| 6,692,518 B2 | 2/2004 | Carson |

(56) References Cited

U.S. PATENT DOCUMENTS

| | | |
|---|---|---|
| 6,692,519 B1 | 2/2004 | Hayes, Jr. |
| 6,695,873 B2 | 2/2004 | Dobak, III et al. |
| 6,695,874 B2 | 2/2004 | Machold et al. |
| 6,699,267 B2 | 3/2004 | Voorhees et al. |
| 6,699,268 B2 | 3/2004 | Kordis et al. |
| 6,702,842 B2 | 3/2004 | Dobak, III et al. |
| 6,704,590 B2 | 3/2004 | Haldeman |
| 6,706,060 B2 | 3/2004 | Tzeng et al. |
| 6,709,448 B2 | 3/2004 | Walker et al. |
| 6,716,236 B1 | 4/2004 | Tzeng et al. |
| 6,719,724 B1 | 4/2004 | Walker et al. |
| 6,723,053 B2 | 4/2004 | Ackerman et al. |
| 6,733,517 B1 | 5/2004 | Collins |
| 6,740,109 B2 | 5/2004 | Dobak, III |
| 6,743,218 B2 | 6/2004 | Maginot et al. |
| 6,746,474 B2 | 6/2004 | Saadat |
| 6,749,625 B2 | 6/2004 | Pompa et al. |
| 6,752,786 B2 | 6/2004 | Callister |
| 6,764,391 B1 | 7/2004 | Grant et al. |
| 6,796,995 B2 | 9/2004 | Pham et al. |
| 6,799,063 B2 | 9/2004 | Carson |
| 6,800,068 B1 | 10/2004 | Dae et al. |
| 6,802,855 B2 | 10/2004 | Ellingboe et al. |
| 6,807,444 B2 | 10/2004 | Tu et al. |
| 6,811,551 B2 | 11/2004 | Dae et al. |
| 6,818,012 B2 | 11/2004 | Ellingboe |
| 6,819,950 B2 | 11/2004 | Mills |
| 6,827,728 B2 | 12/2004 | Ellingboe et al. |
| 6,827,898 B1 | 12/2004 | Fausset et al. |
| 6,872,222 B2 | 3/2005 | Luo et al. |
| 6,878,156 B1 | 4/2005 | Noda |
| 6,887,262 B2 | 5/2005 | Dobak, III et al. |
| 6,887,263 B2 | 5/2005 | Bleam et al. |
| 6,893,454 B2 | 5/2005 | Collins |
| 6,921,198 B2 | 7/2005 | Gruszecki et al. |
| 6,974,463 B2 | 12/2005 | Magers et al. |
| 6,981,945 B1 | 1/2006 | Sarvazyal et al. |
| 7,001,418 B2 | 2/2006 | Noda |
| 7,008,444 B2 | 3/2006 | Dae et al. |
| 7,018,399 B2 | 3/2006 | Dobak, III et al. |
| 7,063,718 B2 | 6/2006 | Dobak, III |
| 7,070,612 B1 | 7/2006 | Collins et al. |
| 7,077,825 B1 | 7/2006 | Stull |
| 7,090,792 B1 | 8/2006 | Balding et al. |
| 7,097,657 B2 | 8/2006 | Noda et al. |
| 7,144,407 B1 | 12/2006 | Lasersohn |
| 7,172,586 B1 | 2/2007 | Dae et al. |
| 7,181,927 B2 | 2/2007 | Collins et al. |
| 7,255,709 B2 | 8/2007 | Walker et al. |
| 7,264,680 B2 | 9/2007 | Gebhart et al. |
| 7,276,046 B1 | 10/2007 | Suzuki et al. |
| 7,278,984 B2 | 10/2007 | Noda et al. |
| 7,287,398 B2 | 10/2007 | Noda et al. |
| 7,294,142 B2 | 11/2007 | Dobak, III et al. |
| 7,300,453 B2 | 11/2007 | Yon |
| 7,311,724 B1 | 12/2007 | Ginsburg |
| 7,311,725 B2 | 12/2007 | Dobak, III |
| 7,361,186 B2 | 4/2008 | Voorhees et al. |
| 7,371,254 B2 | 5/2008 | Dobak, III |
| 7,381,190 B2 * | 6/2008 | Sugrue .............. A61M 25/0017 600/561 |
| 7,407,487 B2 | 8/2008 | Dae et al. |
| 7,425,216 B2 | 9/2008 | Collins |
| 7,458,984 B2 | 12/2008 | Yon et al. |
| 7,491,223 B2 | 2/2009 | Lasheras |
| 7,566,341 B2 | 7/2009 | Keller et al. |
| 7,640,768 B2 | 1/2010 | Noda et al. |
| 7,666,213 B2 | 2/2010 | Freedman, Jr. et al. |
| 7,666,215 B2 | 2/2010 | Callister et al. |
| 7,713,241 B2 | 5/2010 | Cartledge et al. |
| 7,771,460 B2 | 8/2010 | Ginsburg et al. |
| 7,819,835 B2 | 10/2010 | Landy et al. |
| 7,824,436 B2 | 11/2010 | Barbut et al. |
| 7,827,005 B2 | 11/2010 | Kimball |
| 7,842,002 B2 | 11/2010 | Mantle |
| 8,100,880 B2 | 1/2012 | Burnett et al. |
| 8,439,960 B2 | 5/2013 | Burnett et al. |
| 9,238,126 B2 * | 1/2016 | Gerrans .............. A61B 17/24 |
| 2001/0035046 A1 | 11/2001 | Williams |
| 2002/0026094 A1 | 2/2002 | Roth |
| 2002/0033181 A1 | 3/2002 | Groth et al. |
| 2002/0147481 A1 | 10/2002 | Brugger et al. |
| 2003/0018279 A1 | 1/2003 | Rosenblatt |
| 2003/0050621 A1 | 3/2003 | Lebel et al. |
| 2003/0088186 A1 | 5/2003 | Doody |
| 2003/0131844 A1 | 7/2003 | Kumar et al. |
| 2003/0135087 A1 | 7/2003 | Hickle et al. |
| 2004/0087606 A1 | 5/2004 | Voorhees et al. |
| 2004/0102826 A1 | 5/2004 | Lasheras et al. |
| 2004/0122353 A1 | 6/2004 | Shahmirian et al. |
| 2004/0138701 A1 | 7/2004 | Haluck |
| 2004/0158119 A1 | 8/2004 | Osorio et al. |
| 2004/0172116 A1 | 9/2004 | Seifert et al. |
| 2004/0193098 A1 | 9/2004 | Wentling et al. |
| 2004/0231664 A1 | 11/2004 | Lurie et al. |
| 2005/0033391 A1 | 2/2005 | Worthen et al. |
| 2005/0172212 A1 | 8/2005 | Birsa et al. |
| 2005/0177212 A1 | 8/2005 | Njemanze |
| 2005/0203598 A1 | 9/2005 | Becker et al. |
| 2006/0025839 A1 | 2/2006 | Gonzales |
| 2006/0064146 A1 | 3/2006 | Collins |
| 2006/0190066 A1 | 8/2006 | Worthen |
| 2006/0276864 A1 | 12/2006 | Collins |
| 2006/0282039 A1 | 12/2006 | Duong et al. |
| 2006/0293734 A1 | 12/2006 | Scott et al. |
| 2007/0027393 A1 | 2/2007 | Williams et al. |
| 2007/0045188 A1 | 3/2007 | Blanton |
| 2007/0051409 A1 | 3/2007 | Landy, III et al. |
| 2007/0106247 A1 | 5/2007 | Burnett et al. |
| 2007/0173755 A1 | 7/2007 | Alimi et al. |
| 2007/0203552 A1 | 8/2007 | Machold et al. |
| 2007/0225781 A1 | 9/2007 | Saadat et al. |
| 2007/0244446 A1 | 10/2007 | Sundar et al. |
| 2008/0045867 A1 | 2/2008 | Jensen et al. |
| 2008/0077088 A1 | 3/2008 | Collins |
| 2008/0077206 A1 | 3/2008 | Collins |
| 2008/0119757 A1 | 5/2008 | Winter |
| 2008/0119788 A1 | 5/2008 | Winter |
| 2008/0154197 A1 | 6/2008 | Derrico et al. |
| 2008/0200863 A1 | 8/2008 | Chomas et al. |
| 2008/0234619 A1 | 9/2008 | Fausset et al. |
| 2008/0249467 A1 | 10/2008 | Burnett et al. |
| 2008/0255644 A1 | 10/2008 | Carson |
| 2009/0099629 A1 | 4/2009 | Carson et al. |
| 2009/0124937 A1 | 5/2009 | Parks |
| 2009/0131835 A1 | 5/2009 | Voorhees et al. |
| 2009/0240312 A1 | 9/2009 | Koewler |
| 2009/0312676 A1 | 12/2009 | Rousso et al. |
| 2010/0121159 A1 | 5/2010 | Burnett et al. |
| 2010/0204765 A1 | 8/2010 | Hall et al. |
| 2010/0305656 A1 | 12/2010 | Imran et al. |
| 2011/0046547 A1 | 2/2011 | Mantle |
| 2012/0095537 A1 | 4/2012 | Hall et al. |
| 2012/0116487 A1 | 5/2012 | Burnett et al. |

FOREIGN PATENT DOCUMENTS

| | | |
|---|---|---|
| CN | 101327355 A | 12/2008 |
| EP | 0617913 | 10/1994 |
| EP | 0888744 B1 | 1/1999 |
| EP | 2135552 A1 | 12/2009 |
| GB | 2267829 A | 12/1993 |
| JP | 62047335 A | 3/1987 |
| JP | 62-227346 A | 10/1987 |
| JP | 62261366 A | 11/1987 |
| JP | 63166249 U | 10/1988 |
| JP | 64-68275 A | 3/1989 |
| JP | H05-038327 A | 2/1993 |
| JP | 07-275358 A | 10/1995 |
| JP | H08-508176 A | 9/1996 |
| JP | 09-108340 A | 4/1997 |
| JP | 2000-023989 A | 1/2000 |
| JP | 2001-029459 A | 2/2001 |
| JP | 2001-87392 | 4/2001 |

(56) References Cited

FOREIGN PATENT DOCUMENTS

| | | |
|---|---|---|
| JP | 2002-529185 A | 9/2002 |
| JP | 2003-505190 A | 2/2003 |
| JP | 3387602 | 3/2003 |
| JP | 2003533243 | 11/2003 |
| JP | 2004-532655 A | 10/2004 |
| JP | 2004-329763 A | 11/2004 |
| JP | 2004-534590 A | 11/2004 |
| JP | 2004538087 A | 12/2004 |
| JP | 2005211652 | 8/2005 |
| JP | 2005-528160 | 9/2005 |
| JP | 2005527331 A | 9/2005 |
| JP | 2005536277 | 12/2005 |
| KR | 100378358 B1 | 5/2003 |
| WO | WO 93/13718 A1 | 7/1993 |
| WO | WO 98/04191 A1 | 2/1998 |
| WO | WO 99/65552 A1 | 12/1999 |
| WO | WO 00/48670 A1 | 8/2000 |
| WO | WO 00/72779 A2 | 12/2000 |
| WO | WO 01/03606 A2 | 1/2001 |
| WO | WO 01/17471 A1 | 3/2001 |
| WO | WO 01/39819 A2 | 6/2001 |
| WO | WO 01/41708 A2 | 6/2001 |
| WO | WO 01/41858 A2 | 6/2001 |
| WO | WO 01/58509 A1 | 8/2001 |
| WO | WO 02/26175 A1 | 4/2002 |
| WO | WO 02/26176 A1 | 4/2002 |
| WO | WO 02/26285 A2 | 4/2002 |
| WO | WO 02/26307 A1 | 4/2002 |
| WO | WO 02/058606 A1 | 8/2002 |
| WO | WO 03/005908 A2 | 1/2003 |
| WO | WO 03/059218 A1 | 7/2003 |
| WO | WO 03/074107 A2 | 9/2003 |
| WO | WO 03/089031 A1 | 10/2003 |
| WO | WO 2006/060514 A1 | 6/2006 |
| WO | WO 2006/116603 A2 | 11/2006 |
| WO | WO 2009/071094 A2 | 6/2009 |
| WO | WO 2009/071096 A2 | 6/2009 |
| WO | WO 2009/071097 A1 | 6/2009 |
| WO | WO 2009/071098 A2 | 6/2009 |
| WO | WO 2009071095 A2 | 6/2009 |

OTHER PUBLICATIONS

Guerra, et al.; U.S. Appl. No. 13/980,378 entitled "Dual. Thermistor Redundant Temperature Sensor" filed Jul. 18, 2013.

Hall et al.; U.S. Appl. No. 14/040,087 entitled "Method and Apparatus for Inducing Therapeutic Hypothermia," filed Sep. 27, 2013.

Davison et al.; Epidural cooling for regional spinal cord hypothermia during thoracoabdominal aneurysm repair; J. Vasc. Surg.; vol. 20(2); No. 304-10; Aug. 1994 (Abstract Only).

Demling et al.; Initial management of burn patient; (from Burnsurgery.org); Dec. 2004.

Hwang et al.; Peri-operative concerns in thoracic trauma; Bailliére's Clinical Anaesthesiology; vol. 10; No. 1; pp. 123-153; Apr. 1996.

Polderman et al.; Effects of therapeutic hypothermia on intracranial pressure and outcome in patients with severe head injury; Intensive Care Med; vol. 28; pp. 1563-1573; Oct. 2002.

Rutherford et al.; Management of the patient with an open abdomen: techniques in temporary and definitive closure; Curr Probl Surg; vol. 41; pp. 821-876; Oct. 2004.

Sedlak, S. Kay; Hypothermia in trauma: the nurse's role in recognition, prevention, and management; Int'l Journal of Trauma Nursing; ; vol. 1; No. 1; pp. 19-26; Jan. 1995.

Sieh et al.; Intra-abdominal hypertension and abdominal compartment syndrome; Langenbeck's Arch Surg; vol. 386; pp. 53-61; Jan. 2001.

Stover et al.; Treating intracranial hypertension in patients with severe traumatic brain injury during neurointensive care; European Journal of Trauma; 2005(4); pp. 308-330; Jun. 2005.

Burnett et al.; U.S. Appl. No. 13/860,426 entitled "Hypothermia Devices and Methods," filed Apr. 10, 2013.

\* cited by examiner

METHOD AND APPARATUS FOR PRESSURE MEASUREMENT

CROSS REFERENCE TO RELATED APPLICATIONS

This application claims the benefit under 35 U.S.C. 119 of U.S. Provisional Patent Application No. 61/399,298, filed Jul. 9, 2010, titled "Method and Apparatus for Treatment of a Body Cavity or Lumen and Sensing Foley Catheter", and U.S. Provisional Patent Application No. 61/393,794, filed Oct. 15, 2010, titled "Hypothermia Catheter and System". These applications are herein incorporated by reference in their entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention generally relates to measuring pressure within a patient. More specifically, the present invention relates to measuring pressure within cavities and lumens of a patient with an air capsule.

BACKGROUND

Hypothermia has been shown to provide distinct medical benefits to stroke and cardiac arrest patients by limiting the size of the infarction and related tissue injury if initiated soon enough and if the level of cooling is significant enough. Both of these limitations, initiation of and depth of cooling, have made practical application of the technology quite challenging particularly in an ambulance or other emergency settings in the field. Initiation of cooling, for example, is a major issue since most technologies require sophisticated machinery that would be difficult to place in ambulance so the patient, at best, receives the hypothermic benefit some time after they reach the hospital. Of the technologies that can be initiated in the field, though, such as cooling blankets, cooling caps, etc., the depth of cooling is a major issue due to surface area limitations, complications (such as intense shivering response) and patient access issues (once the blanket is on, it may be difficult to access the patient).

Infusion of a hypothermic fluid into a patient, such as into a patient cavity such as the peritoneal cavity, adds additional challenges. The infusion of a large volume of fluid into the patient cavity can increase pressure inside the cavity. High pressures inside the peritoneal cavity can cause problems for the patient, putting the patient's health and well being at risk. Obtaining an accurate measurement of the pressure within the patient can be very difficult in hypothermia applications but is necessary to insure the safety of the patient. Access to the cavity, changing volumes of fluid in the cavity, patient movement, and organs within the cavity all provide challenges for accurate pressure measurement within the patient.

Thus, there exists a need for improved devices for rapidly producing hypothermia to treat stroke, severe cardiac events and related conditions, particularly in the ability to accurately and easily measure pressure within the patient.

SUMMARY OF THE DISCLOSURE

In one embodiment, a pressure measurement system is provided, comprising a catheter, a pressure lumen disposed in the catheter and coupled to a pressure source, a compliant bladder disposed on the catheter, the compliant bladder being in communication with the pressure lumen, a pressure sensor coupled to the pressure lumen and configured to receive a pressure signal from the compliant bladder via the pressure lumen, and a controller configured to receive the pressure signal from the pressure sensor and to control the pressure source to fill the compliant bladder with a volume of gas.

In some embodiments, the controller is configured to execute a priming sequence comprising commanding the pressure source to fill the compliant bladder with a first volume of gas, and after filling the compliant bladder with the first volume of gas, commanding the pressure source to remove a second volume of gas from the compliant bladder so the complaint bladder becomes partially-filled.

In another embodiment, the controller is configured to execute a priming sequence comprising commanding the pressure source to fill the compliant bladder with gas until the complaint bladder reaches a first pressure, and after reaching the first pressure, commanding the pressure source to remove a first volume of gas from the compliant bladder so the complaint bladder becomes partially-filled.

In an additional embodiment, the controller is configured to execute a priming sequence comprising commanding the pressure source to fill the compliant bladder with gas until the complaint bladder reaches a first pressure, and after reaching the first pressure, opening the pressure source to atmospheric pressure for a first amount of time to remove gas from the compliant bladder until the complaint bladder becomes partially-filled.

In some embodiments, the catheter further comprises a fluid infusion lumen and a fluid extraction lumen. In other embodiments, the pressure lumen is disposed in a divider between the fluid infusion lumen and the fluid extraction lumen. In additional embodiments, the pressure lumen is disposed in an interior wall of the catheter.

In one embodiment, a divider between the fluid infusion lumen and the fluid extraction lumen includes ridges to prevent total obstruction of fluid flow in the fluid infusion and extraction lumens during bending or kinking. In another embodiment, the pressure lumen is free floating in the fluid infusion lumen.

In some embodiments, the system further comprises a second pressure lumen coupled to the pressure source and in communication with the compliant bladder. In one embodiment, the pressure lumen and the second pressure lumen are disposed on opposing sides of the catheter.

In some embodiments, the pressure lumen is disposed in an asymmetric wall of the catheter.

In one embodiment, the catheter includes four-extrusions connected end to end, wherein a first extrusion comprises the pressure lumen, and wherein a second, third, and fourth extrusion comprise infusion and extraction lumens. In one embodiment, the infusion lumen occupies approximately one-third of a cross-sectional volume of the catheter.

In some embodiments, the controller is configured to periodically repeat the priming method steps of filling the compliant bladder, then removing air or gas from the bladder until the bladder is partially-filled, to ensure accurate pressure measurements.

Another embodiment further comprises at least one displacement balloon in close proximity to the compliant bladder, the at least one displacement balloon configured to form a void around the compliant bladder.

A method of measuring pressure in a patient is also provided, comprising inserting a pressure measurement catheter into a patient, inflating a compliant bladder of the pressure measurement catheter with gas from a pressure source coupled to the compliant bladder, after the inflating step, removing gas from the compliant bladder so the compliant bladder is partially-inflated, and measuring a pressure of the compliant bladder with a pressure sensor coupled to the compliant bladder to determine a pressure within the patient.

In one embodiment, the removing gas step further comprises removing a pre-determined volume of gas from the compliant bladder. In another embodiment, the removing gas step further comprises opening the compliant bladder to a lower pressure for a period of time to remove gas from the compliant balloon. In some embodiments, the lower pressure is atmospheric pressure.

In one embodiment, the inflating step comprises inflating the compliant bladder with a first volume of air. In another embodiment, the inflating step comprises inflating the compliant bladder to a preset pressure.

In yet another embodiment, the inserting step comprises inserting the pressure measurement catheter into a peritoneal cavity of the patient. In some embodiments, the inserting step comprises inserting the pressure measurement catheter into a stomach of the patient. In one embodiment, the inserting step comprises inserting the pressure measurement catheter into a urinary tract of the patient.

Some embodiments of the method further comprise infusing a fluid into the patient through an infusion lumen of the pressure measurement catheter. The method can further comprise extracting fluid from the patient through an extraction lumen of the pressure measurement catheter.

In some embodiments, the infusing step comprises infusing a hypothermic fluid into the patient.

A method of measuring pressure in a patient receiving therapeutic hypothermia is provided, comprising, inserting a catheter into a peritoneal cavity of the patient, infusing a hypothermic fluid into the patient to achieve therapeutic hypothermia, and measuring a pressure of the peritoneal cavity with an air-filled pressure measurement balloon of the catheter.

DETAILED DESCRIPTION OF THE DISCLOSURE

Devices and methods for measuring pressure are disclosed. More specifically, some embodiments of the present disclosure describe devices and methods for measuring pressure within a patient with a compliant gas-filled bladder or balloon. The compliant gas-filled balloon can be coupled to a gas-filled column located within, for example, a catheter, to measure the pressure inside of patient cavities, organs, lumens, etc.

The present invention overcomes the limitations of the prior art through the use of an air bladder in conjunction with an automated controller to ensure that the volume of air required to perform accurate pressure measurements is maintained within the air capsule.

Figure 1:
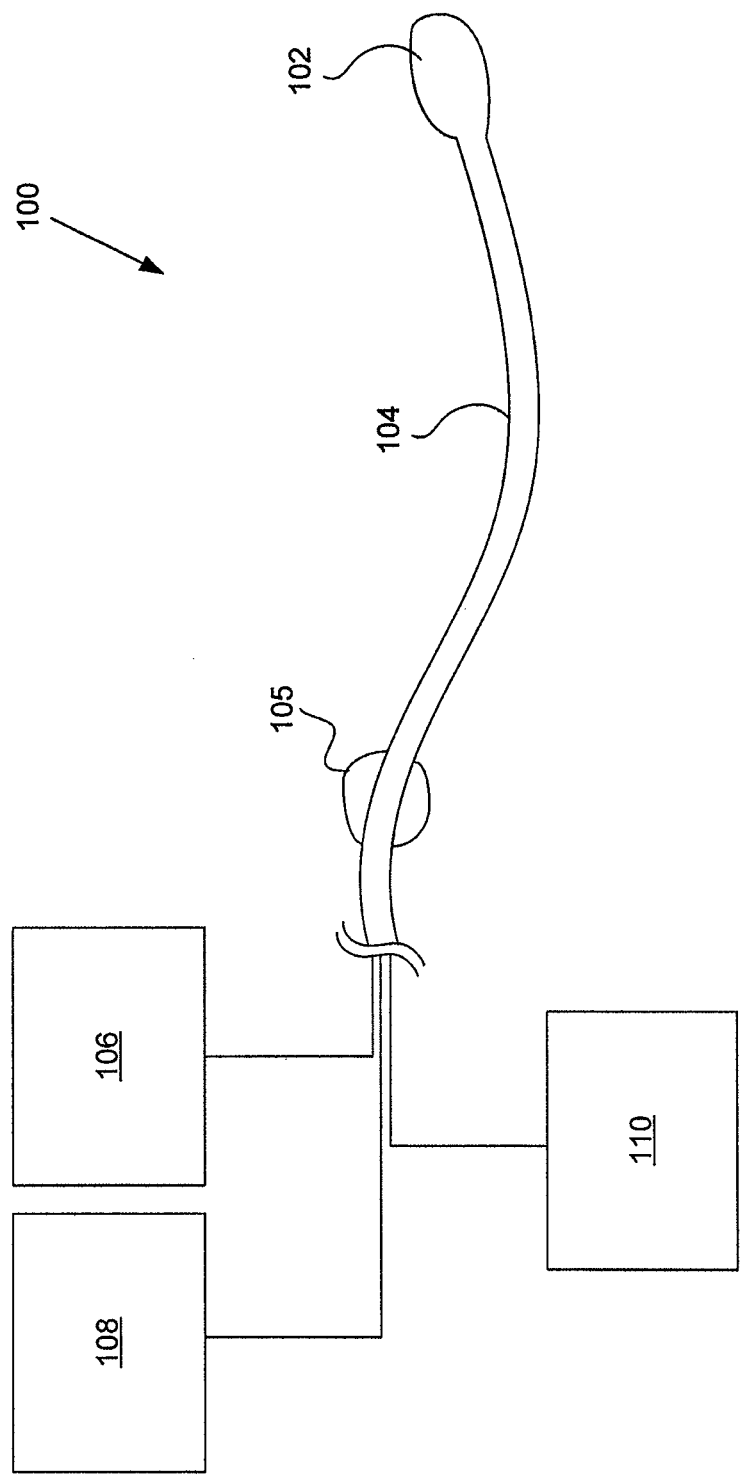
FIG. 1 is one embodiment of a pressure measurement system.

FIG. 1 illustrates one embodiment of a pressure measurement system 100, comprising a compliant balloon 102, catheter 104, a pressure line within the catheter (not shown), pressure sensors 106, pressure source 108, and controller 110. The pressure measurement system 100 can be configured to be inserted into a patient to measure a pressure within the patient. In some embodiments, the system is sized and configured to measure pressure within patient cavities, organs, or lumens. In one embodiment, the system is sized and configured to measure a pressure within the peritoneal cavity of a patient. In another embodiment, the system is sized and configured to measure a pressure within the urinary tract of the patient, such as within the bladder or urethra. In another embodiment, the pressure measurement balloon is inserted into the stomach of the patient.

The compliant balloon 102 may comprise any compliant material. Within this disclosure, the compliant balloon may be referred to as a balloon, bladder, membrane, or other similar term. The balloon can comprise any compliant, flexible, non-porous material configured to expand or retract with inflation and deflation of a gas or fluid. The balloon 102 may comprise a thermoset or thermoplastic polymer, silicon, latex, or any other compliant material used in medical balloon applications, for example. In some embodiments, "rigid" polymers can be beneficial for pressure measurement applications. In some embodiments, the balloon that can be collapsed for insertion and removal. In one embodiment, the balloon may be tacked down by folding and setting of the balloon or through application of vacuum to collapse the balloon radially. Alternatively, the tip of the balloon may reversibly engage the tip of the catheter and may disengage during air inflation of the capsule.

An important feature is for the balloon to have a sufficient volume for a pressure measurement application. Sufficiency of the volume of the balloon is determined by the ratio of the pressure line volume to the balloon volume. In some embodiments, the volume of the balloon at least 15% of the total volume in the pressure lines. In one embodiment, the volume of the balloon is approximately 8-12 cc and the volume of the pressure lines is approximately 11-16 cc, however larger volumes may provide less sensitivity to fill volume.

Referring still to FIG. 1, one or more balloons 102 may be used in the pressure measurement system. In the illustrated embodiment, the balloon is positioned at a distal end of the catheter 104. However, in other embodiments, the balloon may be located at any location along the length of the catheter, so long as it can be positioned within the patient to collect pressure information. The balloon 102 may be any shape, such as spherical, ribbed, elongated, or with splines. An elongated balloon is preferred because it can have a large volume but still groom or deflate down to a small diameter for placement into the patient and removal from the patient. In some embodiments, the balloon can have a length of approximately 4-8 cm. The balloon may inflate to a diameter of approximately 1-3 cm in a pressure measuring configuration, and may deflate down to a total diameter of approximately 0.1-1 cm in a delivery configuration. It should be noted that, in the delivery configuration, the balloon diameter is limited to the size of the catheter being used.

The balloon may also be asymmetric in a way that it expands preferentially on the side of the catheter, aligning with holes for air communication. This helps ensure that the balloon will not interfere with other functions of the catheter which may occur on the opposite side of the catheter, such as fluid flow, temperature measurement, or optical or ultrasound assessment of surrounding tissues.

Catheter 104 can include an independent pressure lumen for communication between the balloon 102 and pressure sensors 106. The pressure lumen is not illustrated in FIG. 1 as it is disposed within the catheter, but will be illustrated and described in more detail below. The pressure lumen couples the balloon 102 to pressure sensors 106, providing an air/gas column between the balloon and the sensors. The catheter 104 can further include fluid infusion and/or extraction lumens for delivering fluid to a patient and/or removing fluid from the patient. In some embodiments, the catheter can include separate infusion and extraction lumens. Each of the infusion and extraction lumens may further include infusion and extraction ports positioned at specified points along the catheter, to allow for communication between the infusion/extraction lumens and the outside of the catheter. Further details on a catheter system with suitable infusion and extraction lumens and ports are described in U.S. patent application Ser. No. 12/702,165, titled "Method and Apparatus for Inducing Therapeutic Hypothermia," filed Feb. 8, 2010.

The catheter may have features to aid in correct depth setting of the pressure sensing balloon including, a retention balloon 105 proximal to the balloon 104 that can be used as an anchor to the inside of the patient. In another embodiment, a bend in the catheter proximal to the balloon 104 that can be configured to anchor the catheter inside the cavity. The bend may be flexible enough to pass through an access port (not shown) but offer enough resistance to straightening to allow the user to feel the bend against the inside of the patient when applying a removing force to the catheter.

In some embodiments, the connection between the catheter and the remainder of the system is done with a single motion. The user can push the catheter into a receiving end until they reach a certain force or until there is audible (click) or tactile feedback. Tactile feedback may be provided by a detent feature, such as a swaged extrusion passing by an O-ring, or by a feature bottoming out into a tapered shaft.

The catheter connection may also complete an electrical circuit or press a button, allowing the controller 110 to know that the catheter has been connected. The connection may have a resistor of a particular value to indicate an identifying piece of information such as lot #, model #, or calibration. In other embodiments, the catheter may also have an RFID chip in it to convey information to the controller 110 about information such as lot #, model #, or calibration.

In other embodiments, the catheter may have a fuse or other feature that can be disabled at the end of treatment for identification of used devices.

Figure 2A:
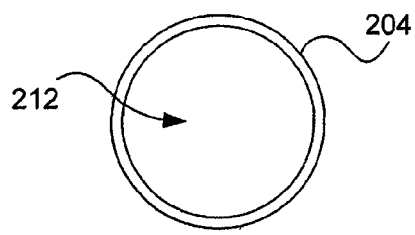
FIGS. 2A-2J illustrate various embodiments of a pressure measurement catheter.
Figure 2B:
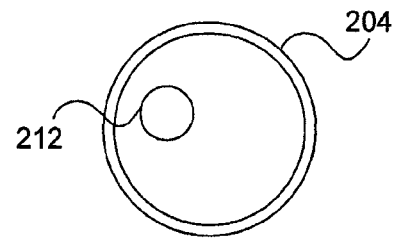

FIG. 2A is one embodiment of a cross sectional view of catheter 204, which can be catheter 104 of system 100 in FIG. 1. In FIG. 2A, the interior of catheter 204 can comprise pressure lumen 212. The pressure lumen may connect to the controller and/or pressure sensors as an individual connection (e.g., luer connection) or as part of a step that connects multiple connections, fluid and/or electrical to the controller and/or pressure sensors. For applications in which the pressure lumen and balloon are filled with air, the pressure lumen can be as small as 0.024" ID and function as required. FIG. 2B is another embodiment of catheter 204 and pressure lumen 212. In FIG. 2B, the pressure lumen does not occupy the whole interior of the catheter, but rather, is its own separate lumen. The embodiment of FIG. 2B shows the pressure lumen 212 being disposed off-center within the catheter. However, in other embodiments, the pressure lumen can be disposed in the center of the catheter, or even positioned adjacent to the interior wall of the catheter. In some embodiments, the pressure lumen may be floating within an already-existing lumen of the catheter.

Figure 2C:
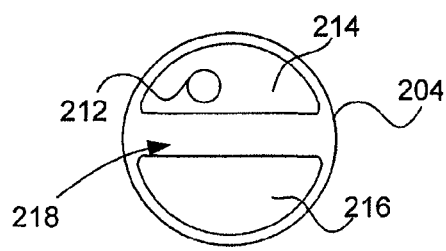

In some embodiments, the pressure lumen may be part of a multi-lumen extrusion within the catheter of the pressure measurement system. As described above, one or more of these lumens may be used for infusion or extraction of fluids to and from a patient. In the embodiment of FIG. 2C, catheter 204 can include infusion lumen 214 and extraction lumen 216. The pressure lumen 212 can be disposed within either of the lumens. In FIG. 2C, the pressure lumen 212 is shown as a floating lumen within the infusion lumen 214. The lumens can be separated by a divider 218, of any desired thickness. For example, a thicker divider 218 may increase the cross-sectional strength of the catheter, increasing bend or kink resistance, at the expense of reducing the total volume of fluid that can be infused/extracted by the catheter.

Figure 2D:
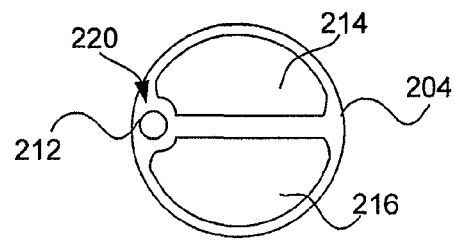
Figure 2E:
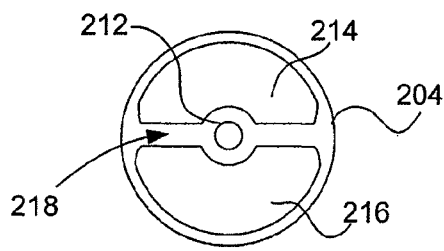

FIG. 2D illustrates an embodiment where the pressure lumen 212 is embedded inside a wall 220 of the catheter. FIG. 2E illustrates an embodiment where the pressure lumen is embedded inside the divider 218 of the catheter. In the embodiment of FIG. 2E, positioning the pressure lumen in the center of the catheter allows the catheter to flex symmetrically during use, and provides for some kink protection because the central location of the pressure lumen holds the infusion and extraction lumens at least partially open during flexure.

Figure 2F:
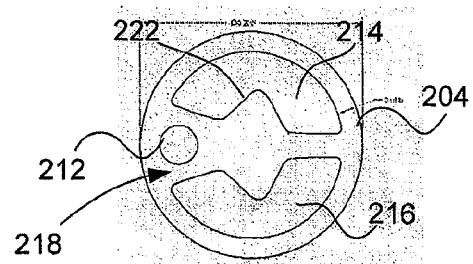

FIG. 2F illustrates yet another embodiment, wherein the pressure lumen 212 is embedded inside of wall 220 of the catheter, and the divider 218 includes ridges 222 to prevent total obstruction of flow within the infusion/extraction lumens during bending or kinking.

Figure 2G:
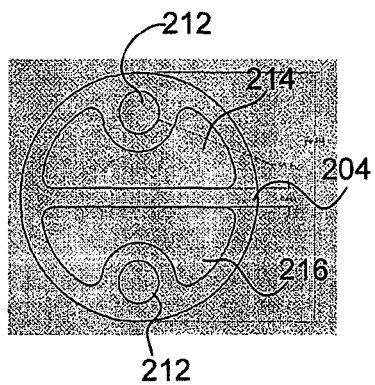

In FIG. 2G, the catheter includes two pressure lumens 212 for pressure measurement redundancy. Both pressure lumens may be disposed in exterior walls of the catheter, as shown.

In some embodiments, the pressure lumens can be positioned across from another in the catheter, for example, spaced 180 degrees apart. This can allow the catheter to bend uniformly. In this embodiment, the dual pressure lumens can also serve to prevent total occlusion of the flow path in the infusion or extraction lumens 214 and 216 during bending or kinking. The dual pressure lumens may communicate with the same pressure measurement balloon, or separate balloons located on opposite sides are at different locations along the length of the catheter.

Figure 2H:
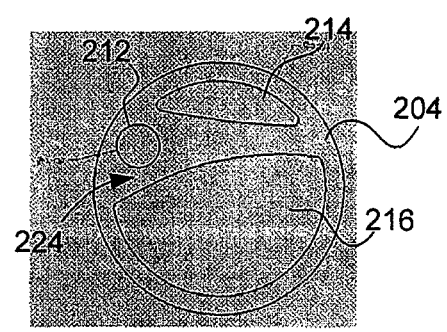

In another embodiment, as shown in FIG. 2H, the pressure lumen 212 can be disposed in an asymmetric wall 224. This design allows for formation of a large extraction lumen 216 (relative to the infusion lumen 214). In some embodiments, a reinforcing structure, such as a coil or other device, can be used in the extraction lumen or within the walls of the catheter to aid in preventing kinking.

Figure 2I:
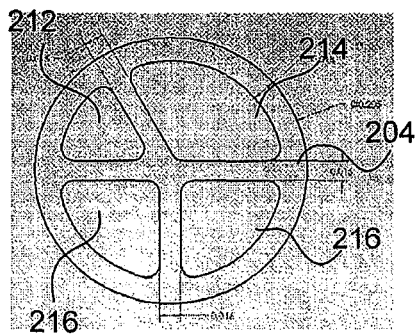

In FIG. 2I, the catheter 204 can include four extrusions to provide for excellent kink resistance without needing to add a separate kink-reducing structural component. In this embodiment, the two lower extrusions can be used as extraction lumens 216, and the upper right extrusion can be infusion lumen 214. The final extrusion can be used as the pressure lumen 212. In the illustrated embodiment, the infusion lumen 214 occupies approximately 120 degrees of the catheter, and the pressure lumen occupies approximately 60 degrees of the catheter.

Figure 2J:
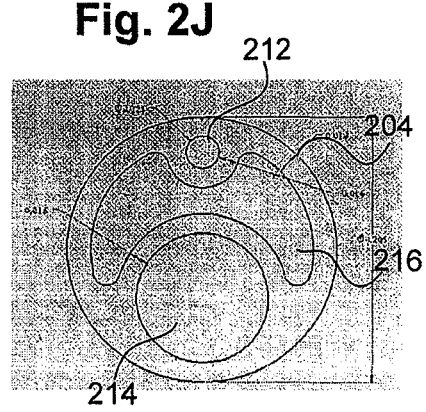

In the embodiment of FIG. 2J, the infusion lumen 214 can be a round lumen, the extraction lumen 216 can wrap around the infusion lumen, and the pressure lumen can be disposed in the wall of the catheter 204 next to the extraction lumen. This embodiment also provides for excellent kink resistance while allowing for efficient fluid infusion and removal.

In some embodiments, the pressure lumen comprises a different material than the rest of the catheter. While it is often desirable for the catheter to be flexible, in some embodiments, the pressure lumen can be made out of a more rigid material, or the infusion or extraction lumens may have a braided material in the wall (stainless steel for example) to make the catheter wall stiffer. This stiffness aids in the prevention of kinking and isolates the pressure signal from pressure in the other lumens of the catheter. Depending on the relationship in volume between the pressure lumen and the measurement balloon, this level of isolation may not be necessary because the lumen wall deflection may create negligible volume change.

In the embodiments described above, the ratio of cross sectional area between the infusion lumen and the extraction lumen can vary from 1:1 to 1:2, respectively, but other ratios can also be used. Also, in any of the embodiments described above, the catheter or even the individual lumens can include anti-kinking devices, including but not limited to a structure within one or more of the catheter lumens or walls such as a coil, a braid, or an extrusion in a V, Y, or + shape.

In some embodiments, the catheter can be designed in a way that enables it to groom down in the region of the balloon to a smaller diameter to allow for fitment of an access port over the catheter. In one embodiment, the catheter grooms down to fit through a 5 mm access port. In one embodiment, the catheter necks down to a smaller outer diameter distal to the end of the infusion lumen. The balloon can then reside distal to the termination of the infusion lumen. In some embodiments, the catheter may have three lumens on the proximal end (e.g., infusion, extraction, and pressure), but reduce the number of lumens along its length. For example, after the infusion holes, the infusion lumen could end. After the pressure lumens/balloon, the pressure lumen could end. This can be accomplished with stop-lumen extrusion technology, by reflow of extrusion material, or by butt-joining different extrusion designs to each other.

Referring back to FIG. 1, the system 100 can further include one or more pressure sensors 106. The pressure sensor(s) 106 can be any type of pressure sensor configured to measure air or fluid pressure, as known in the art. In some embodiments, a pressure sensor is included inside controller 110, however they are described and illustrated separately in this disclosure to ease in the description. The pressure sensors may be reusable or disposable. In one embodiment, the sensors are a reusable component in the controller. The advantage of using pressure sensors coupled to the pressure lumen and balloon with air is that the sensors can be at a different elevation than the balloon without having an offset in the pressure signal, owing to the negligible density of air. During a medical procedure in which a catheter is inserted into a patient and the balloon is not visible, more accurate pressure measurements can be made without having to worry about aligning the elevation of external pressure sensors with a (sometimes unknown) balloon depth.

Temperature compensation to account for differences in temperature between the pressure sensor location and the balloon location has not been found to be necessary in the pressures and temperatures for therapeutic hypothermia with peritoneal lavage. However in some embodiments, for added accuracy, temperature can be measured in the catheter in the vicinity of the balloon with a temperature sensor (thermistor, thermocouple, optical sensor, etc.).

Referring still to FIG. 1, the system 100 can also include a pressure source 108 to provide gas or air pressure to the pressure lumen and balloon. In some embodiments, the pressure source is a manual pressure source, such as a syringe or bellows. In other embodiments, the pressure source is automated, such as a pump. Any kind of automated pump can be used to move gas, air, or fluid into the pressure lumen and balloon, such as a diaphragm, syringe, gear, bellows, peristaltic pump, etc. In other embodiments, a compressed air supply, such as in a hospital, can be used to fill the pressure lumen and balloon with air.

When air is the material used to fill the balloon, the design may have great sensitivity to the presence of fluid contaminants in the pressure measurement lumen. With small diameter pressure lumens, the surface tension of fluid can prevent small volumes of fluid from moving within the lumen thereby damping, diminishing, or even eliminating a pressure signal from reaching the external sensors. Thus, various embodiments can mitigate against fluid blockage of the pressure lumen. In one embodiment, the pressure lumen can be lined with a hydrophobic material that will reduce the attraction between an undesired fluid and the pressure lumen wall. In another embodiment, the addition of a surfactant or similar chemical can reduce the surface tension of the fluid in the pressure lumen. In another embodiment, a hydrophilic fiber can be disposed within the pressure lumen. The hydrophilic fiber can have a smaller diameter than that of the pressure lumen, so gas or air can still travel along the pressure lumen. Fluid will be attracted to the fiber and be less likely to wet the walls of the pressure lumen, thereby leaving space for the pressure signal to travel. In one embodiment, if the hydrophilic fiber becomes saturated with fluid, the system can include an indicator or a circuit coupled to the control system to alert that the fiber is full. For example, a saturated fiber could close a circuit to set off an alarm in the control system, or alternatively, the fiber could change color when saturated and be checked occasionally by a medical worker (e.g., a nurse). In another embodiment, the pressure lumen can include a combination of a wick and hydrophobic coating on the inner wall of the lumen.

In yet another embodiment, the pressure lumen may be hydrophobic and have an irregular cross-section involving one or more projections in one or more directions. This irregular lumen will be resistant to obstruction by water droplets which will want to form spherical bodies based on the properties of the surface tension of water in the presence of a hydrophobic material. With droplets forming in the center of the lumen, said projections will resist obstruction and provide a continuous air channel from proximal end to the distal end of the catheter. Obstruction by a fluid formation in the catheter may also be prevented by the use of intermittent evacuation of the balloon and pressure lumen. This method may be used on its own or in conjunction with any of the other embodiments outlined above and entails intermittently evacuation the balloon and the pressure lumen to remove fluid excess into a proximal fluid collection reservoir or water scavenger. In combination with the automated balloon priming to appropriately refill the balloon, this feature will allow for intermittent removal of accumulated water which, if not removed, could potentially overwhelm the lumen.

Additional solutions to this issue of fluid in the pressure lumen are disclosed. In one embodiment, a pump can move air through the pressure lumen at all times that the catheter is disconnected to keep the pressure lumen free of fluid. In another embodiment, the catheter includes separate pressure lumen and infusion lumen connectors, rather than a single connection that connects to the rest of the system with a single motion. In another embodiment, the pressure lumen can have a sleeve, sheath, cap, or other protective mechanism over the proximal end of the pressure lumen that is configured to slide out of the way upon connection to the rest of the system. In one embodiment, a cap can be spring loaded so as to engage whenever the pressure lumen is disconnected from the system. In another embodiment, a stylet can be placed in the pressure lumen of the catheter and be removed just prior to connection with the system.

In FIG. 1, the system further includes a controller 110. In many embodiments, the controller can be configured to automatically control one or more parameters related to pressure measurement, calibration, and infusion or extraction of fluid to and from a patient. It should be appreciated that controller 110 can also be configured to perform a variety of operations including communicating with external devices including devices linked over the Internet; wireless peripheral devices; data operations; and various power management functions.

Controller 110 can include one or both of analog or digital circuitry for performing its control operations. The controller will also typically be configured to receive one or more inputs, such as from pressure sensors 106. Typically, the controller will include a computer processor which is configured to execute one or more electronic instruction sets contained within a software module, which can be stored in memory onboard the controller. Additionally, controller 110 can be configured to be programmed by the user (e.g., using a user interface or by an external device such as a wireless device) to allow for manual control of one or more operations of the system (e.g., infusion rate, extraction rate, pressure line calibration, etc).

Figure 3:
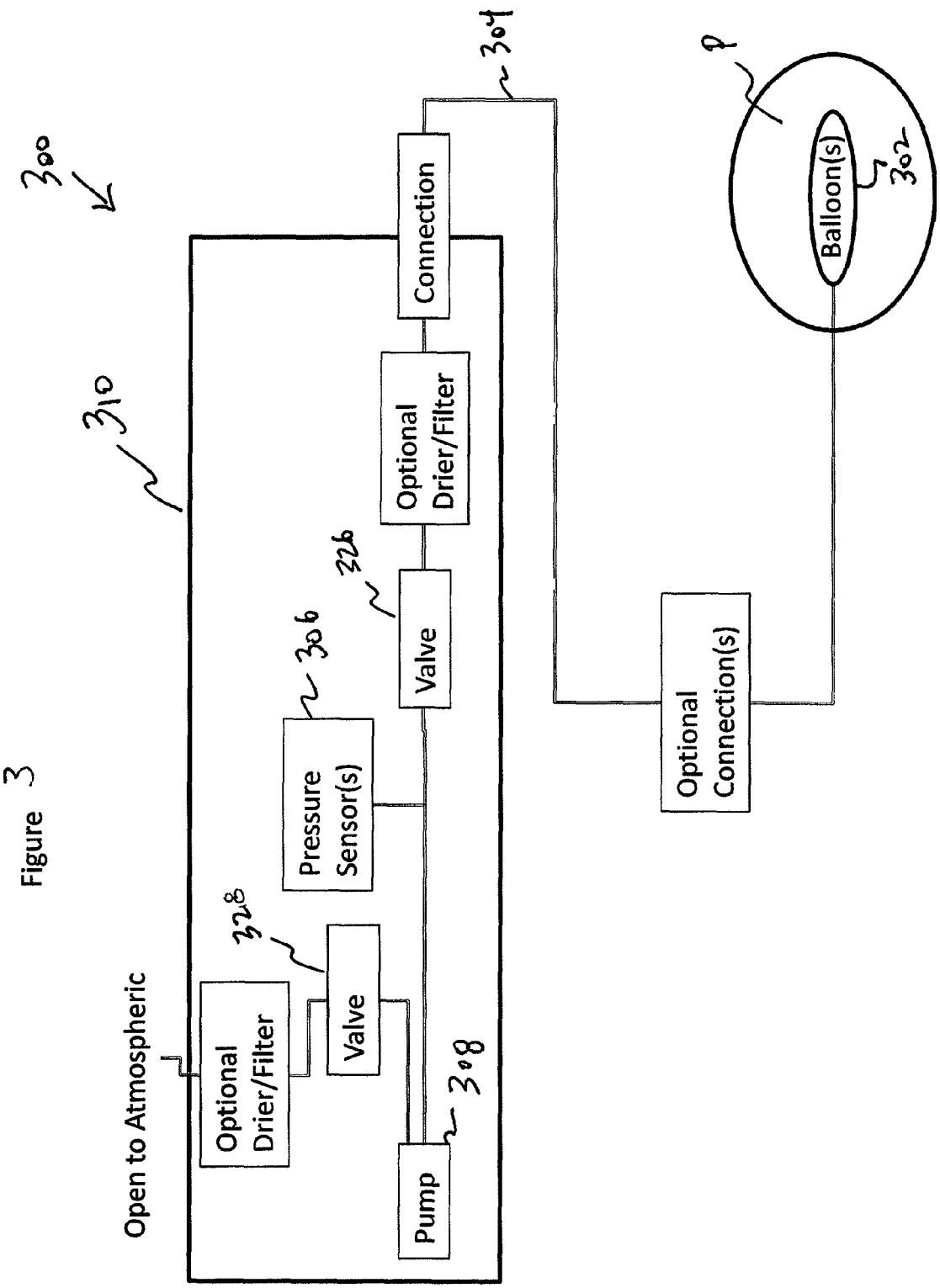
FIG. 3 is another embodiment of a pressure measurement system.

Methods of measuring pressure with the systems described herein will now be described, with reference to FIGS. 1 and 3. The pressure measurement system of FIG. 1, particularly balloon 102, catheter 104, pressure sensors 106, pressure source 108, and controller 110, can correspond to balloon 302, catheter 304, pressure sensors 306, pressure source 308, and controller 310 of FIG. 3. In one embodiment, pressure sensors 306 can be zeroed to atmospheric pressure while the system is in a standby mode, before use. Next, the catheter 304 can be placed into a space within the patient P for which a pressure measurement is desired with the aid of an access device. After removal of the access device, the catheter can be connected to the controller 310 and/or pressure sensors 306. In some embodiments, as described above, the controller is configured to automatically detect when the catheter is connected to the controller.

In one embodiment, upon connection of the catheter, the controller can close a first valve 326 disposed between the pressure source 308 (e.g., a pump) and the catheter 304, isolating the pressure source 308 from the catheter 304. In one optional embodiment, the system can evacuate the balloon and pressure lumen prior to closing the first valve. The controller can then open a second valve 328 disposed between the pressure source and the outside to open the pressure source up to atmosphere and enable the pressure source to fill with atmospheric air. Once the pressure source is filled with air, the first valve can open to connect the pressure source and catheter again.

Next, the pressure source can fill the pressure lumen of the catheter and balloon 302 with air/gas. In some embodiments, the controller 310 fills the balloon 302 until the balloon reaches a specified pressure or volume (based on the volume of the balloon). In some embodiments, when the specified pressure or volume is reached it serves as an indicator to the controller that the balloon is properly coupled to the controller and rest of the system. In some embodiments, the specified pressure of volume is the pressure or volume to fully fill the balloon with air/gas. Thus, in one embodiment, the pressure source fills the pressure lumen and balloon with air or gas until the balloon is fully inflated.

In one embodiment, the controller can pause for a set period of time and perform a leak test to evaluate the system for leaks in the balloon or catheter connections. The leak test can ensure that the balloon is viable and ready for use in pressure measurement. The leak test can determine that the balloon is leak free based on expected pressure and/or volume characteristics.

Next, in one embodiment, the controller can remove a predetermined amount of air or gas from the balloon 302 to make the balloon partially-filled. The amount of gas/air removed from the balloon can be pressure-controlled or volume-controlled. In one embodiment, a bellows pump displaces a fixed amount to remove a fixed volume of air from the balloon. Additionally, the removal of air or gas from the balloon can be time based, for example the balloon could be vented to atmospheric pressure for a specified amount of time (e.g., for fractions of seconds to seconds). Finally, once the proper amount of gas or air is in the balloon and pressure lumen, the first valve 326 between the pressure source 308 and the catheter 304 can be closed, rendering the system 300 ready for pressure measurement. Even with bellows/syringe type pumps, closing the first valve is beneficial because it decreases the air volume of the sensing system, making the pressure in the system more sensitive to changes in the catheter balloon.

During use, the controller 310 may periodically evaluate the balloon 302 and the catheter connections by refilling the balloon to a set pressure. Additionally, the controller can perform a leak test prior to using the system for a pressure measurement by observing the air pressure signal for drift. Retesting the system is very useful in long procedures, where there is potential for manipulation and/or damage to the catheter between pressure measurements.

In some embodiments, the controller can automatically maintain a desired pressure or volume in the balloon 302. As with any air or gas filled balloon, air loss or pressure loss can always be a problem. However, this air or pressure loss is unpredictable and can vary based on the environment and type of procedure in which the balloon is used. The present system can overcome this limitation by intermittently filling the balloon 302 to a desired pressure or volume of gas/air. In some embodiments, after filling to the desired volume or pressure, the controller can automatically remove a specified amount of gas or air from the balloon to make the balloon partially-filled or more compliant. In another embodiment, the controller can completely evacuate the balloon at specified intervals during a procedure, then fill the balloon to the optimal pressure or volume or the leak test pressure or volume in the manner described above.

The controller may also test the connection between the balloon and the pressure sensor by analyzing the pressure signal for the pressure cycles associated with patient respirations. If the balloon was not inflated or was over-inflated, these respirations would not be evident. Respiration and patient activity can create variations in pressure with magnitudes up to 100 mm Hg (coughs). Air pressure signals occur when the balloon has a nominal amount of air in it and that volume can compress and expand in response to changes in surrounding pressure. If a balloon is under-inflated, the baseline pressure of the cavity may be sufficient to collapse the volume of air in the balloon, eliminating the air/gas pressure signal since no further compression of the air/gas can take place. A similar problem occurs if the catheter balloon is over inflated. Cavity pressures and fluctuations below the catheter balloon pressure will not affect the pressure in the balloon and thus go un-measured. For example, if the catheter balloon was inflated to 200 mmHg, the 100 mm Hg pressure from a cough would not compress the catheter balloon and generate a pressure signal.

The system may have an expected range of volumes of air that are required to fill the balloon. This information can be used to detect whether or not there is a kink in the line between the sensors and the balloon. For example, if pressure readings from the pressure sensors indicate that the pressure in the balloon is at the expected value, but a lower volume of air or gas was filled in the balloon to attain that value, then the controller can determine that there is a kink in the pressure lumen.

Referring again to FIGS. 1, FIGS. 2A-2J, and FIG. 3, in one embodiment the catheter of the present disclosure may be used in methods to measure pressure in a patient while inducing and maintaining therapeutic hypothermia in the patient. While this disclosure is directed to the pressure measurement aspect of the procedure, further details and description regarding the therapeutic hypothermia aspect of the procedure may be found in the U.S. patent application Ser. No. 12/702,165 referenced above.

In a first step of the method, the catheter is inserted into a peritoneal cavity of a patient. Next, the cavity pressure measurement catheter is connected to the controller 108, primed, and made ready to measure pressure in the manner described above. Specifically, the pressure source can fully inflate the balloon with air or gas, then remove a predetermined volume of fluid from the balloon until it is partially-inflated. An initial pressure reading can be taken with the balloon 102 of system 100.

Next, controller 110 can initiate infusion of a hypothermic fluid into the peritoneal cavity to induce therapeutic hypothermia in the patient. As the fluid is being infused into the patient, the pressure sensors can acquire pressure signals from the pressure lumen and balloon 102 indicating a pressure within the peritoneal cavity. In some embodiments, the pressure measurements are taken in real time. In other embodiments, the pressure measurements are taken at predetermined intervals.

Figure 4:
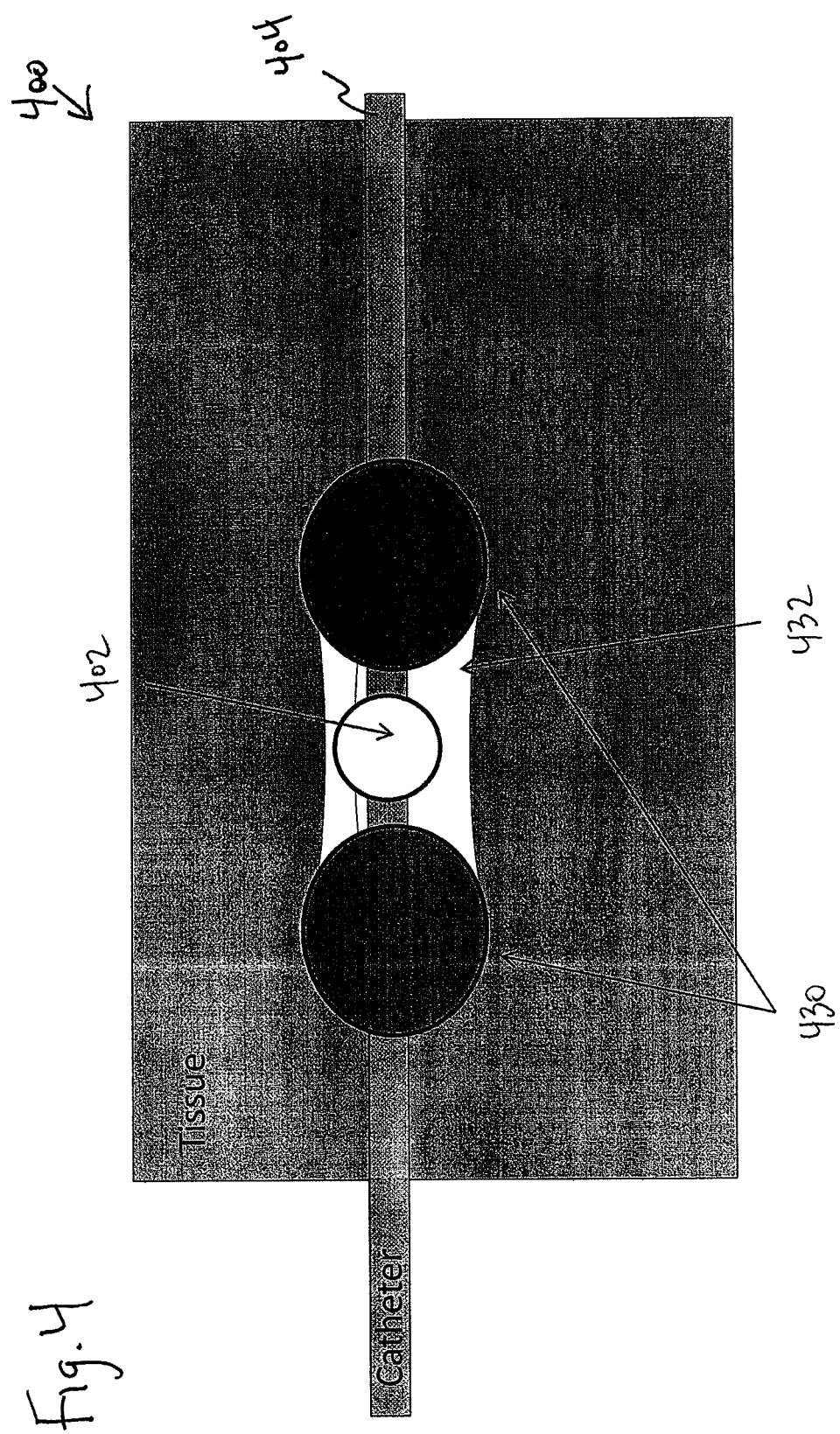
FIG. 4 is one embodiment of a pressure measurement system with displacement balloons adjacent to or in close proximity to a measurement balloon.

In another embodiment of the pressure measurement system, referring to FIG. 4, the system can include a mechanism for protecting the pressure measuring balloon from interference by foreign objects touching the balloon. In FIG. 4, catheter 404 of system 400 can further include displacement balloons 430 adjacent to or in close proximity to pressure measurement balloon 402. After insertion of the catheter into a patient cavity or lumen, displacement balloons 430 can be inflated to form a void 432 around the pressure measurement balloon 402. The balloon can then be primed and readied for pressure measurement following the steps listed above. The displacement balloons form a void around the pressure measurement balloon to protect the balloon from touching foreign objects, such as organs within a dry patient cavity. One benefit of the displacement balloons is that they can be deflated to a small diameter during insertion of the patient so as to be constrained through the access device.

Figure 5:
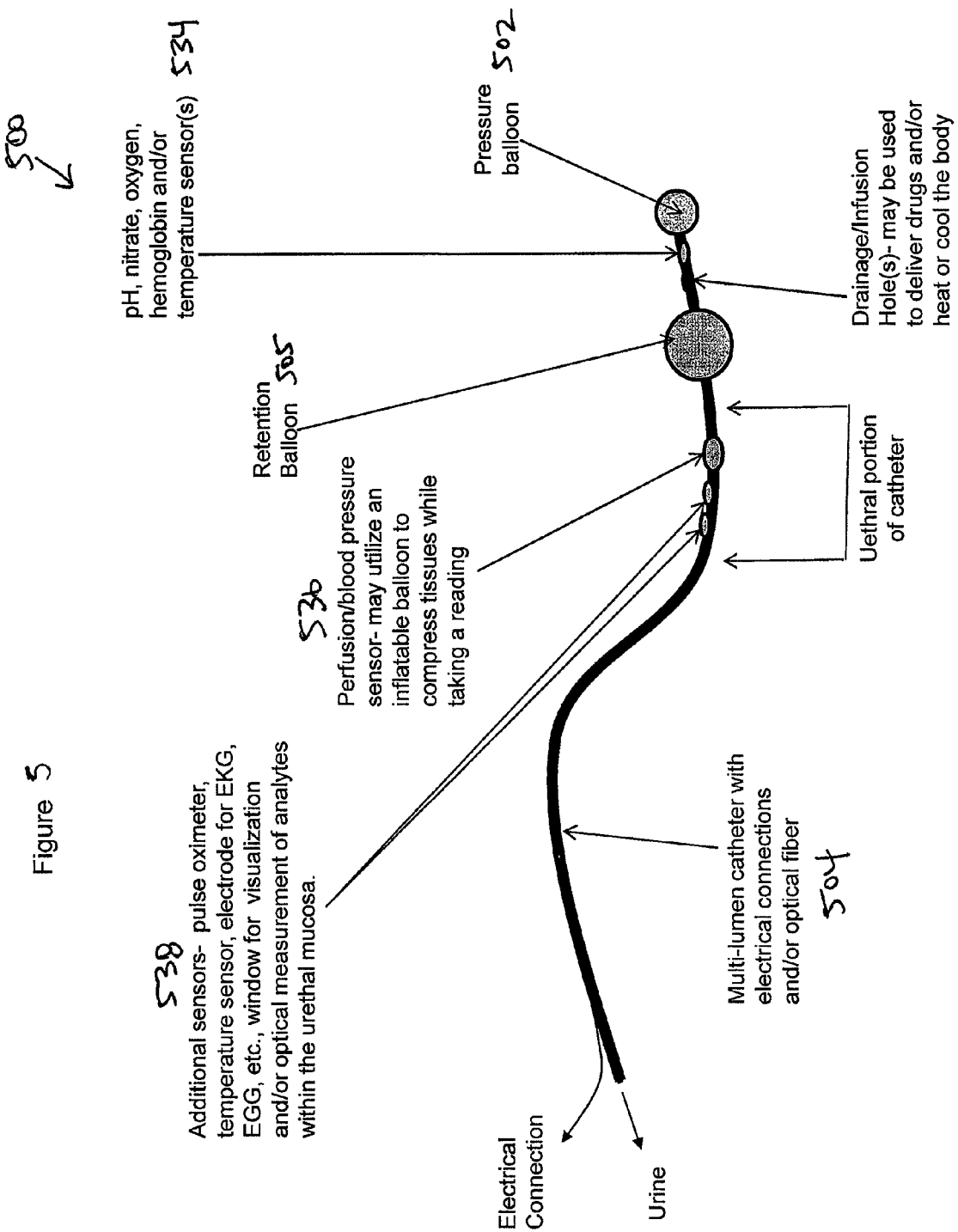
FIG. 5 is one embodiment of a Foley-style pressure measurement system.

Referring now to FIG. 5, in another embodiment, a pressure measurement system 500 can incorporate a modified Foley catheter specially configured to measure pressure and other parameters in the urinary tract, such as within the urethra and/or bladder. As such, the catheter 504 of FIG. 5 can be sized and configured to be inserted into the urinary tract of a patient. In FIG. 5, the catheter 504 can include a balloon 502 coupled to a pressure lumen, as described above. Additionally, the catheter can include a retention balloon 505 configured to hold the catheter in place. In some embodiments, the catheter includes sensors 534 disposed between the pressure balloon and the retention balloon, the sensors configured to measure pH, nitrate, oxygen, hemoglobin, and/or temperature.

In alternative embodiments, other portions of the Foley catheter may be configured to sense one or more of the following parameters with sensors 536 and 538: urine pH, urine oxygen content, urine nitrate content, respiratory rate, heart rate, perfusion pressure of bladder wall and/or urethra, temperature inside bladder and/or urethra, electrocardiography via sensors on the bladder wall and/or urethra, respiratory volume, respiratory pressure, peritoneal pressure, urine glucose, blood glucose via urethral mucosa and/or bladder mucosa, urine proteins, urine hemoglobin, blood pressure, and any other physiologic parameter that can be measure in urine or from the urethra and/or bladder wall.

In one embodiment, the catheter can sense a minimum of two parameters, but may be limited to a single parameter for focused applications (i.e., respiratory rate in a patient in respiratory distress). The respiratory rate, relative tidal volume, peritoneal pressure, heart rate and/or relative cardiac output may be measured simultaneously, as well, by connecting a balloon with a flaccid wall or semi-tense wall to an external pressure sensor via a lumen that may be filled with liquid and/or gas. These parameters may also be measured, alone or in concert with other parameters, through the use of pressure measurement modalities other than the external pressure sensor. These may include: a deflecting membrane inside of the catheter, MEMs technology, a catheter-based sensor and/or other embodiments.

In some embodiments, as well, the catheter may include a blood pressure sensing element which may take many forms, one of which involves an inflatable member (either a separate balloon or, ideally, a balloon in fluid communication with the retention and/or pressure sensing balloon) which may be optically analyzed as it is inflated to determine at which pressure the vessels within the urethra are blanched and blood flow is stopped. This will provide a highly accurate reading of the perfusion pressure of the urethra which provides an indication of both overall blood pressure and vascular resistance. This implantable perfusion pressure device may be used to provide early detection and/or monitoring of a variety of disease conditions including sepsis, shock, hemorrhage, etc. and can usually detect these conditions in the early stages. This methodology may also be used to detect perfusion pressure in other areas of the body with an intermittently inflatable member and optical detection of blood flow and/or presence of blood.

Other modalities may be used to detect that the tissue has been blanched, as well, with the critical component being that of the intermittent inflation within the lumen, body cavity or bodily tissues to provide the compression of the vasculature. Relative cardiac output and relative tidal volume may be calculated, as well, based on the deflection of the pressure sensor and/or other force gauge. If sampled frequently enough (i.e., 2 Hz or faster), the respiratory excursion can not only be counted, but they can be quantified in a relative manner to the amplitude of the excursions at the time of catheter placement. Larger excursions mean either heavier breathing or, in the setting of an upward drift in the baseline, a higher peritoneal pressure. The small peaks on the oscillating respiratory wave, caused by the pumping heart, may be tracked as well, and the amplitude of this wave may be used, in the setting of a relatively constant peritoneal pressure, to determine the relative cardiac output.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A pressure measurement system, comprising:
    a catheter;
    a pressure lumen disposed in the catheter and coupled to a pressure source;
    a compliant bladder disposed on the catheter, the compliant bladder being in communication with the pressure lumen;
    a retention balloon positioned proximal to the compliant bladder and configured to anchor the catheter within a patient body;
    a pressure sensor coupled to the pressure lumen and configured to receive a pressure signal from the compliant bladder via the pressure lumen; and
    a controller configured to receive the pressure signal from the pressure sensor and to control the pressure source to fill the compliant bladder with a volume of gas.

2. The system of claim 1 wherein the controller is programmed with instructions to execute a priming sequence, the instructions comprising:
    commanding the pressure source to fill the compliant bladder with a first volume of gas; and
    after filling the compliant bladder with the first volume of gas, commanding the pressure source to remove a second volume of gas from the compliant bladder so the complaint bladder becomes partially-filled.

3. The system of claim 1 wherein the controller is programmed with instructions to execute a priming sequence, the instructions comprising:
    commanding the pressure source to fill the compliant bladder with gas until the complaint bladder reaches a first pressure; and
    after reaching the first pressure, commanding the pressure source to remove a first volume of gas from the compliant bladder so the complaint bladder becomes partially-filled.

4. The system of claim 1 wherein the controller is programmed with instructions to execute a priming sequence, the instructions comprising:
    commanding the pressure source to fill the compliant bladder with gas until the complaint bladder reaches a first pressure; and
    after reaching the first pressure, opening the pressure source to atmospheric pressure for a first amount of time to remove gas from the compliant bladder until the complaint bladder becomes partially-filled.

5. The system of claim 1 wherein the catheter further comprises a fluid infusion lumen and a fluid extraction lumen.

6. The system of claim 5 wherein the pressure lumen is disposed in a divider between the fluid infusion lumen and the fluid extraction lumen.

7. The system of claim 5 wherein the pressure lumen is disposed in an interior wall of the catheter.

8. The system of claim 7 wherein a divider between the fluid infusion lumen and the fluid extraction lumen includes ridges to prevent total obstruction of fluid flow in the fluid infusion and extraction lumens during bending or kinking.

9. The system of claim 5 wherein the pressure lumen is free floating in the fluid infusion lumen.

10. The system of claim 1 further comprising a second pressure lumen coupled to the pressure source and in communication with the compliant bladder.

11. The system of claim 10 wherein the pressure lumen and the second pressure lumen are disposed on opposing sides of the catheter.

12. The system of claim 1 wherein the pressure lumen is disposed in an asymmetric wall of the catheter.

13. The system of claim 1 wherein the catheter includes four-extrusions connected end to end, wherein a first extrusion comprises the pressure lumen, and wherein a second, third, and fourth extrusion comprise infusion and extraction lumens.

14. The system of claim 13 wherein the infusion lumen occupies approximately one-third of a cross-sectional volume of the catheter.

15. The system of claim 2 wherein the instructions further comprise periodically repeating the priming sequence ensure accurate pressure measurements.

16. The system of claim 3 wherein the instructions further comprise periodically repeating the priming sequence to ensure accurate pressure measurements.

17. The system of claim 4 wherein the instructions further comprise periodically repeating the priming sequence to ensure accurate pressure measurements.

18. The system of claim 1 further comprising at least one displacement balloon in close proximity to the compliant bladder, the at least one displacement balloon configured to form a void around the compliant bladder.

19. The system of claim 1 wherein the controller is further configured to automatically detect when the catheter is connected to the controller.

20. The system of claim 19 wherein the controller is configured to detect when a predetermined pressure or volume is reached by the compliant bladder as an indication of the catheter being properly connected to the controller.

* * * * *